(12) United States Patent
Chen (10) Patent No.: US 11,419,960 B2
(45) Date of Patent: Aug. 23, 2022

(54) PORTABLE UV-SANITIZING BOX

(71) Applicant: Jian Chen, Yuanjiang (CN)

(72) Inventor: Jian Chen, Yuanjiang (CN)

( * ) Notice: Subject to any disclaimer, the term of this patent is extended or adjusted under 35 U.S.C. 154(b) by 0 days.

(21) Appl. No.: 17/712,202

(22) Filed: Apr. 4, 2022

(65) Prior Publication Data

US 2022/0218859 A1   Jul. 14, 2022

(51) Int. Cl.
*A61L 2/26* (2006.01)
*A61L 2/10* (2006.01)

(52) U.S. Cl.
CPC .. *A61L 2/26* (2013.01); *A61L 2/10* (2013.01)

(58) Field of Classification Search
None
See application file for complete search history.

(56) References Cited

U.S. PATENT DOCUMENTS

| 2011/0243789 A1 | 10/2011 | Roberts |
| 2016/0158395 A1 | 6/2016 | Hughes |
| 2021/0113723 A1 | 4/2021 | Malinowski et al. |

FOREIGN PATENT DOCUMENTS

| CN | 214908229 U | * 11/2021 |
| TW | I601431 B | * 10/2017 |

* cited by examiner

*Primary Examiner* — Andrew Smyth
(74) *Attorney, Agent, or Firm* — Rumit Ranjit Kanakia (57) ABSTRACT

The present disclosure provides a portable UV-sanitizing box, providing a lower shell, an upper shell hinged to the lower shell, a sterilizing assembly having an ultraviolet ray lamp assembly arranged on the upper shell, a first conductive component arranged on the lower shell for electrically connecting to the first printed circuit board assembly, a first magnetic member adjacent to the first conductive component mounted on the lower shell, a second conductive component arranged on the upper shell for electrically connecting to the ultraviolet ray lamp assembly, a second magnetic member corresponding to the first magnetic member adjacent to the second conductive component mounted on the lower shell, the second magnetic member and the first magnetic member are magnetically attracted to each other.

15 Claims, 12 Drawing Sheets

PORTABLE UV-SANITIZING BOX

FIELD OF THE DISCLOSURE

The present disclosure relates to the field of sanitizing devices using Ultra Violet (UV) light. More specifically, the disclosure relates to a small, hands free, portable, rechargeable, UV-C light emitting sanitizing box.

BACKGROUND

Personal hygiene care products such as dentures, braces, and tooth retainer are placed in the UVC sanitizing device, which is more convenient to carry around. U.S. Pat. No. 5,029,252 discloses an apparatus for disinfection of lavatory instruments, medical instruments or the like, through ultraviolet radiation, wherein the instruments are arranged within a housing in combination with a mounting plate and irradiated by a light source which generates UV-radiation.

Generally, when the UV light sterilization box is performing sterilization work, the magnetic induction switch is used to detect the opening and closing status of the UV sterilization and disinfection box for controlling the opening and closing of the ultraviolet sterilization lamp, which may prevent accidental opening and avoid ultraviolet rays from causing damage to the eyes. However, the arrangement of the magnetic induction device requires additional component arrangement, and the process is relatively complicated. Moreover, the sterilization box with only UV light cannot effectively improve the sterilization efficiency.

Therefore, it is necessary to provide a lithium battery for solving the issues.

SUMMARY OF THE INVENTION

In view of this, the present disclosure is designed to provide a portable UV-sanitizing box to improve safety and disinfection efficiency.

The portable UV-sanitizing box has a lower shell having a first outer housing, a carrying plate, a tray configured to carry items to be sterilized, an upper shell hinged to the lower shell, having a second outer housing and a second inner housing, a sterilizing assembly has an ultraviolet ray lamp assembly arranged on the upper shell, a switching button, and a first printed circuit board assembly arranged on the lower shell, a first conductive component arranged on the lower shell has two first conductive terminals for electrically connecting to the first printed circuit board assembly, and a first magnetic member adjacent to the first conductive component is mounted on the lower shell, a second conductive component arranged on the upper shell has two second conductive terminals for electrically connecting to the ultraviolet ray lamp assembly, a second magnetic member corresponding to the first magnetic member adjacent to the second conductive component mounted on the lower shell, and the second magnetic member and the first magnetic member are magnetically attracted to each other. When the upper shell and the lower shell are snapped together, the first conductive member and the second conductive member are in contact with each other and are configured to be in electrical communication, so that the sterilizing assembly works. When the upper shell is opened, the first conductive member and the second conductive member are not in electrical contact with each other.

In another aspect, the first magnetic member is located between the two first conductive terminals, and the second magnetic member is located between the two second conductive terminals.

In another aspect, the first magnetic member is offset from the connecting line between the two first conductive terminals.

In another aspect, the carrying plate has a first mounting portion protruding inwardly relative to the edge of the lower housing, the first conductive component and the first magnetic member are mounted on the first mounting portion.

In another aspect, the tray includes a concave first accommodating cavity and a recess for accommodating the first mounting portion.

In another aspect, an adsorption cavity is provided on the tray, an activated carbon is arranged in the adsorption cavity, and the adsorption cavity is communicated with the first accommodating cavity of the tray.

In another aspect, the tray is made of plastic, silicone, rubber materials.

In another aspect, the switching button is exposed on the upper shell and is electrically connected to a second printed circuit board assembly of the second conductive component.

In another aspect, a first inner housing is provided between the carrier board and the tray for loading activated carbon.

In another aspect, an adsorption cavity is provided on the first inner housing, an activated carbon is loaded in the adsorption cavity.

In another aspect, the number of adsorption chambers is at least two, which are arranged symmetrically.

In another aspect, a fan element is installed on a surface of the carrier board away from the upper shell for promoting internal air circulation of the sanitizing box.

In another aspect, the carrier plate has an air outlet which is matched with the fan element.

In another aspect, a ventilation slot is provided on the the carrier plate for communicating with the air outlet.

In another aspect, the first inner housing is provided with an air circulation slits for communicating with ventilation slot and the adsorption cavity.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiment.

DETAILED DESCRIPTION OF THE PREFERRED EMBODIMENTS

Embodiments of the present disclosure will be described in detail in conjunction with the drawings. It should be noted that the figures are illustrative rather than limiting. The figures are not drawn to scale, do not illustrate every aspect of the described embodiments, and do not limit the scope of the present disclosure.

It should be noted that when a component is considered to be "connected" to another component, it can be directly connected to another component or a central component can be present between two components at the same time. When a component is considered to be "provided" another component, it may be arranged directly on another component or possibly with a centered component.

Unless otherwise defined, all technical and scientific terms used herein have the same meaning, which is used in the description of the present disclosure to describe specific embodiments and is not intended to limit the disclosure. The term "or/and" used here includes any and all combinations of one or more of the associated listed items.

Referring to FIGS. 1 to 11, a portable UV-sanitizing box 100 according to an embodiment of the present disclosure is shown. The portable UV-sanitizing box 100 is provided with a accommodating cavity, and the accommodating cavity is used for personal appliances such as dentures, braces, braces, toothbrush heads, earrings and the like. The size of the sterilizing box 100 in the present disclosure may be packed into a satchel or a clothes pocket, and is very convenient to carry.

Figure 1:
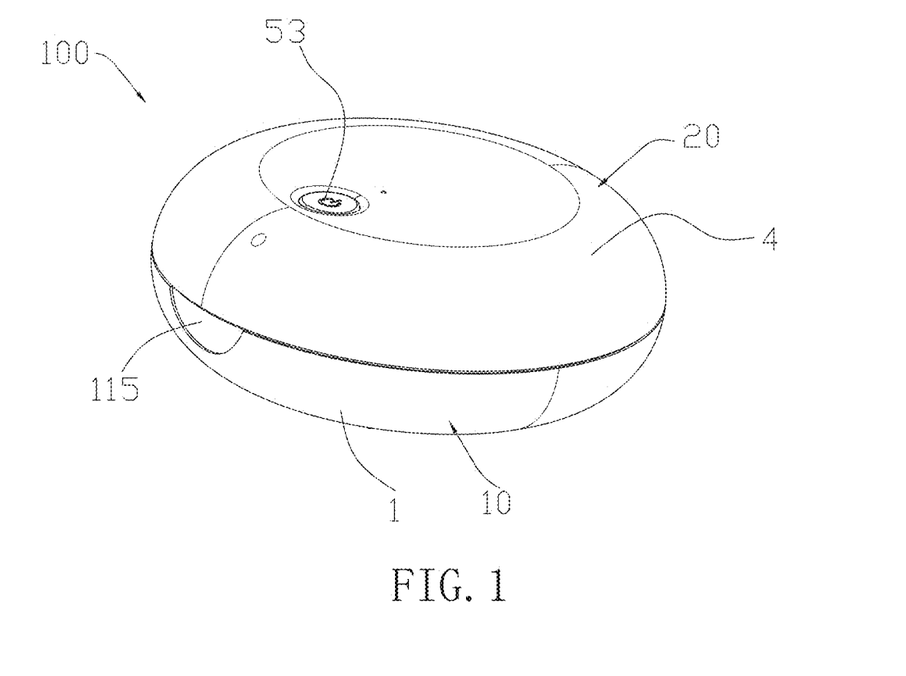
FIG. 1 is an isometric view of an portable UV-sanitizing box in accordance with an exemplary embodiment of the present disclosure.
Figure 2:
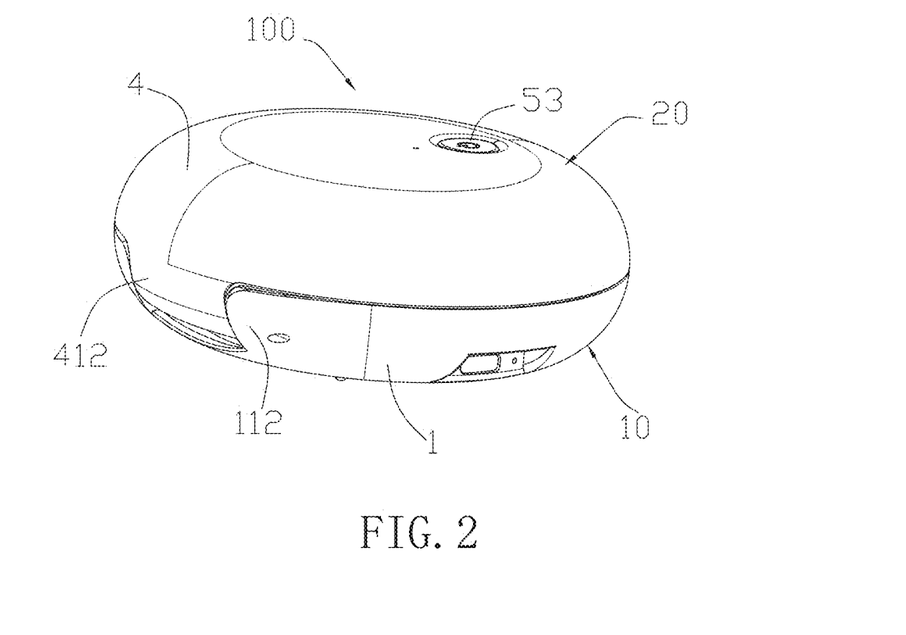
FIG. 2 is an isometric view of the portable UV-sanitizing box in FIG. 1, viewed from another aspect.
Figure 3:
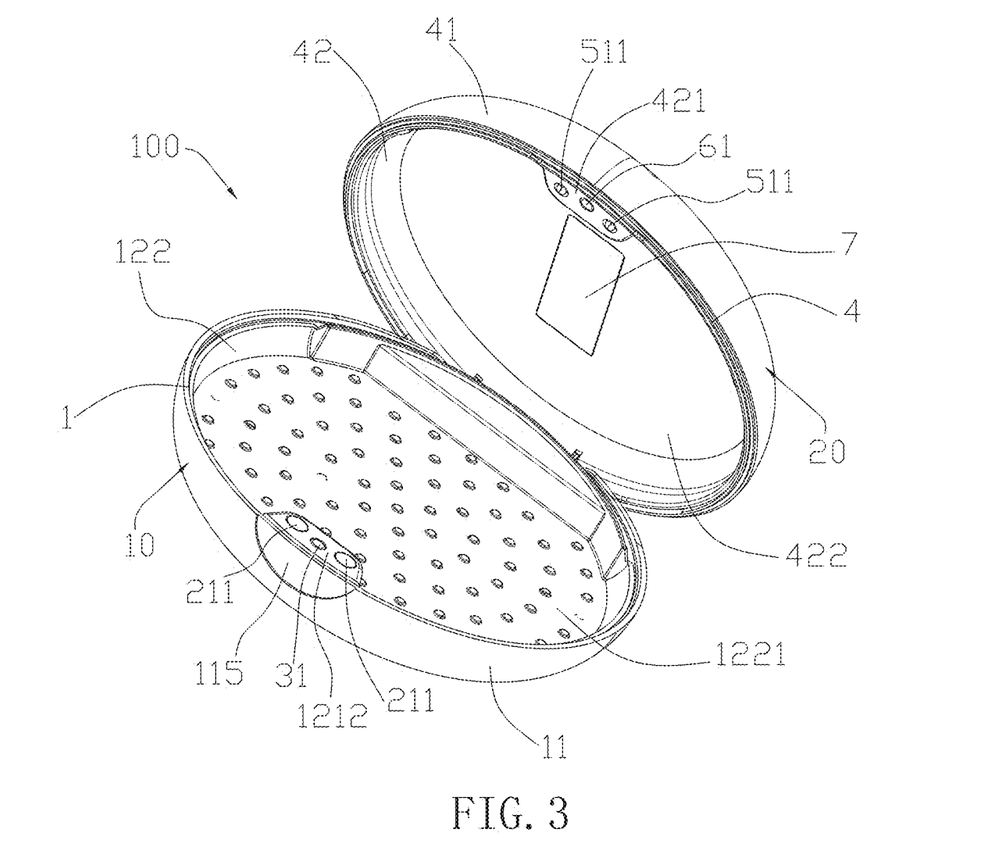
FIG. 3 is an isometric view of the portable UV-sanitizing box being opened in FIG. 2.
Figure 4:
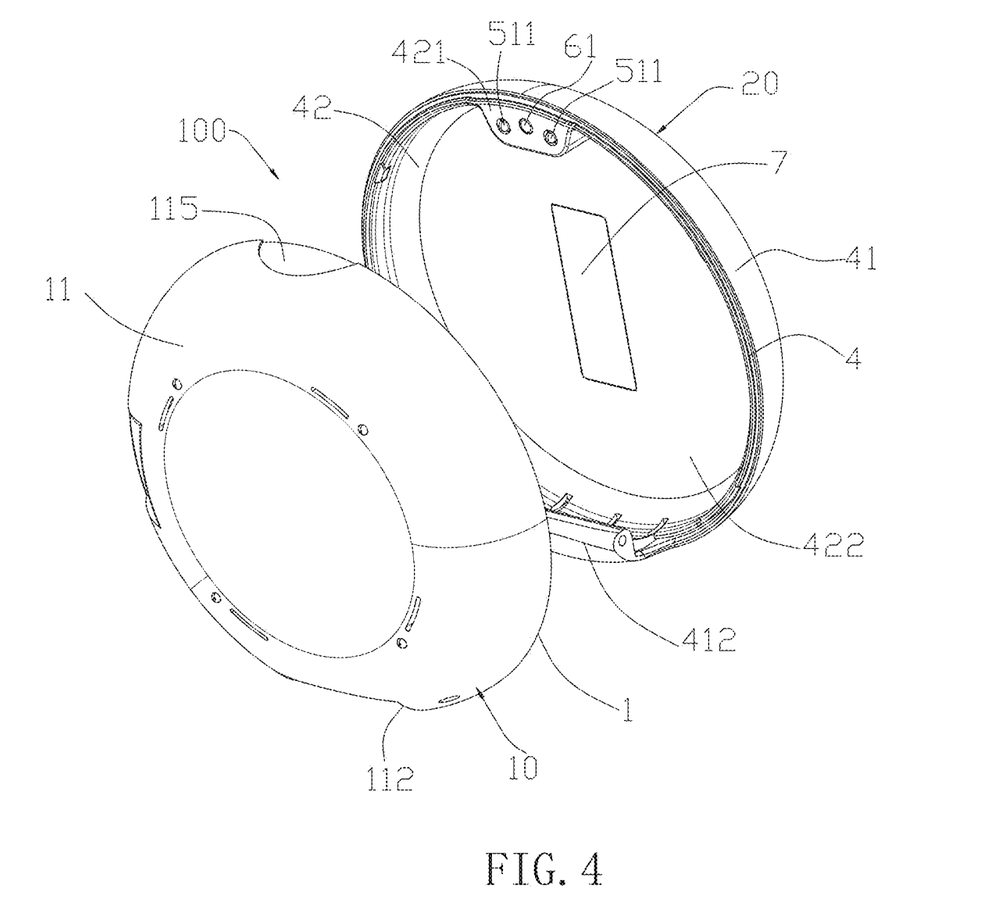
FIG. 4 is an isometric view of the portable UV-sanitizing box in FIG. 1. With an upper cover and a lower cover being disengaged, viewed from another aspect.

The UV-sanitizing box 100 includes a lower shell 10, an upper shell 20 and a sterilizing assembly 30. The sterilizing assembly 30 is an ultraviolet ray lamp assembly. The lower shell 10 and the upper shell 20 are pivotally arranged to open or cover the accommodating cavity. When the lower shell 10 and the upper shell 20 are opened and separated, the accommodating cavity is exposed, and the sterilizing assembly 30 is not electrically connected. When the lower shell 10 and the upper shell 20 are closed, the accommodating cavity is shielded, and the sterilizing assembly 30 may work in electrical conduction. In other embodiments, the lower shell 10 and the upper shell 20 may also be slidably connected to realize opening and closing arrangement. For example, the lower shell 10 is provided with a slide rail, and the upper shell 20 is provided with chute to matching the slide rail. In other embodiments, the lower shell 10 and the upper shell 20 are in other connection ways, so that when opened, the lower shell 10 and the upper shell 20 are spaced apart and not connected each other.

Figure 5:
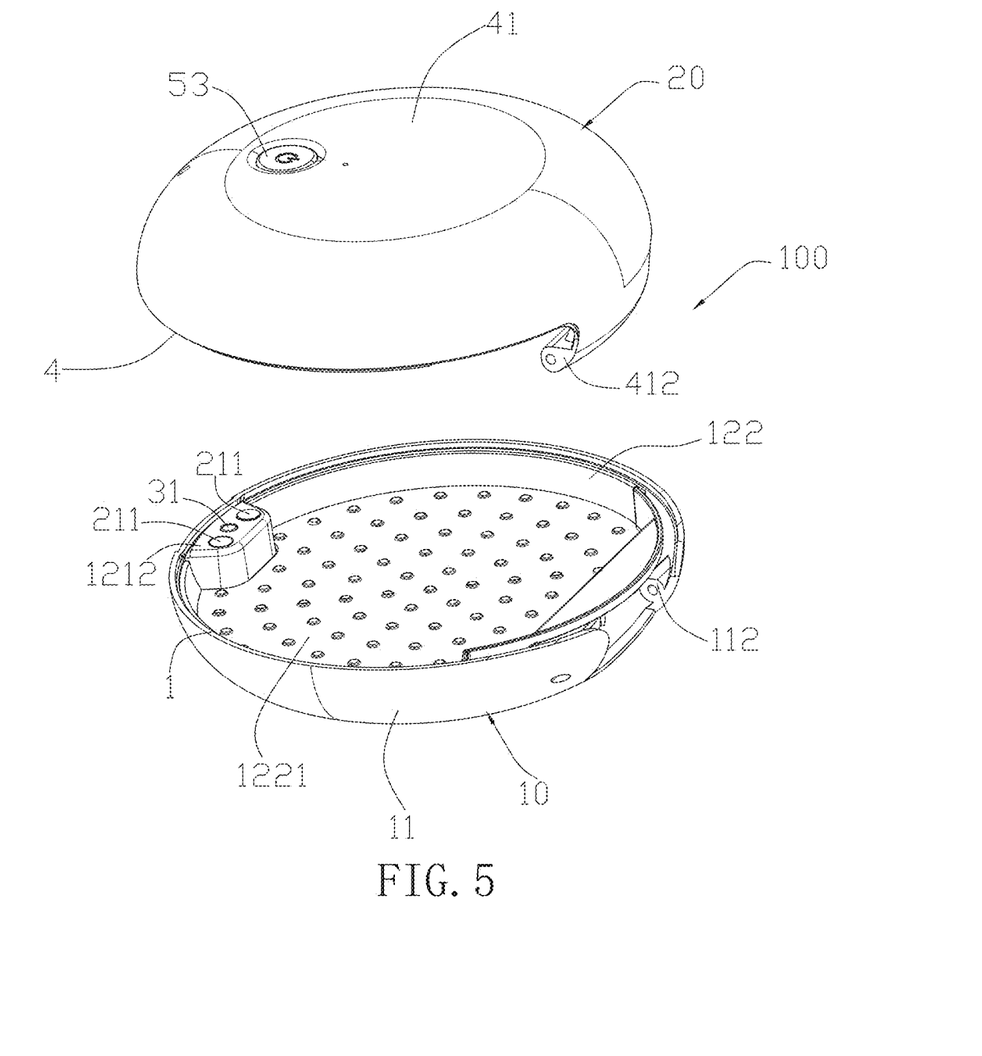
FIG. 5 is an isometric exploded view of a part of the portable UV-sanitizing box in FIG. 4, viewed from another aspect.
Figure 6:
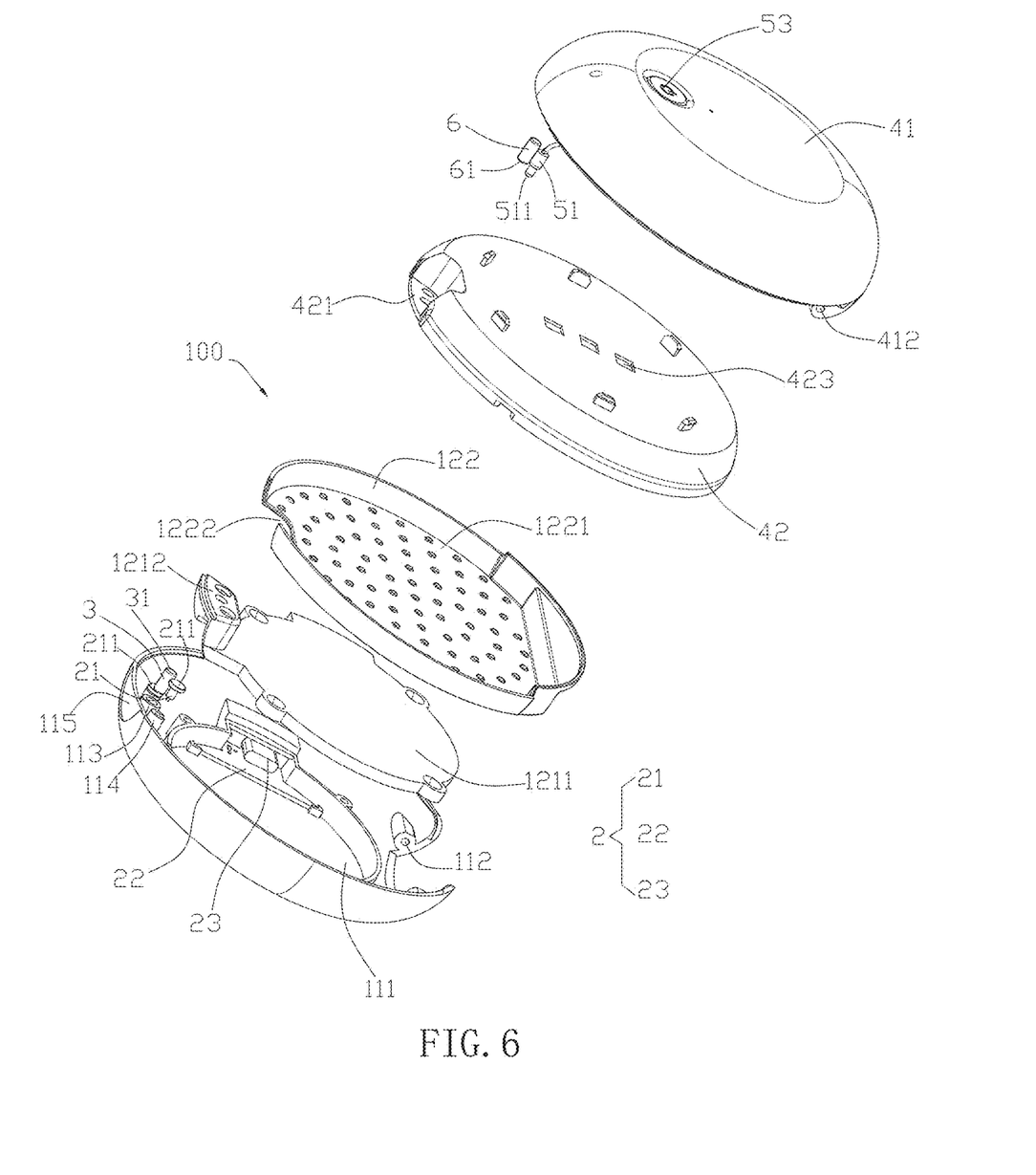
FIG. 6 is an isometric exploded view of the portable UV-sanitizing box in FIG. 5.
Figure 7:
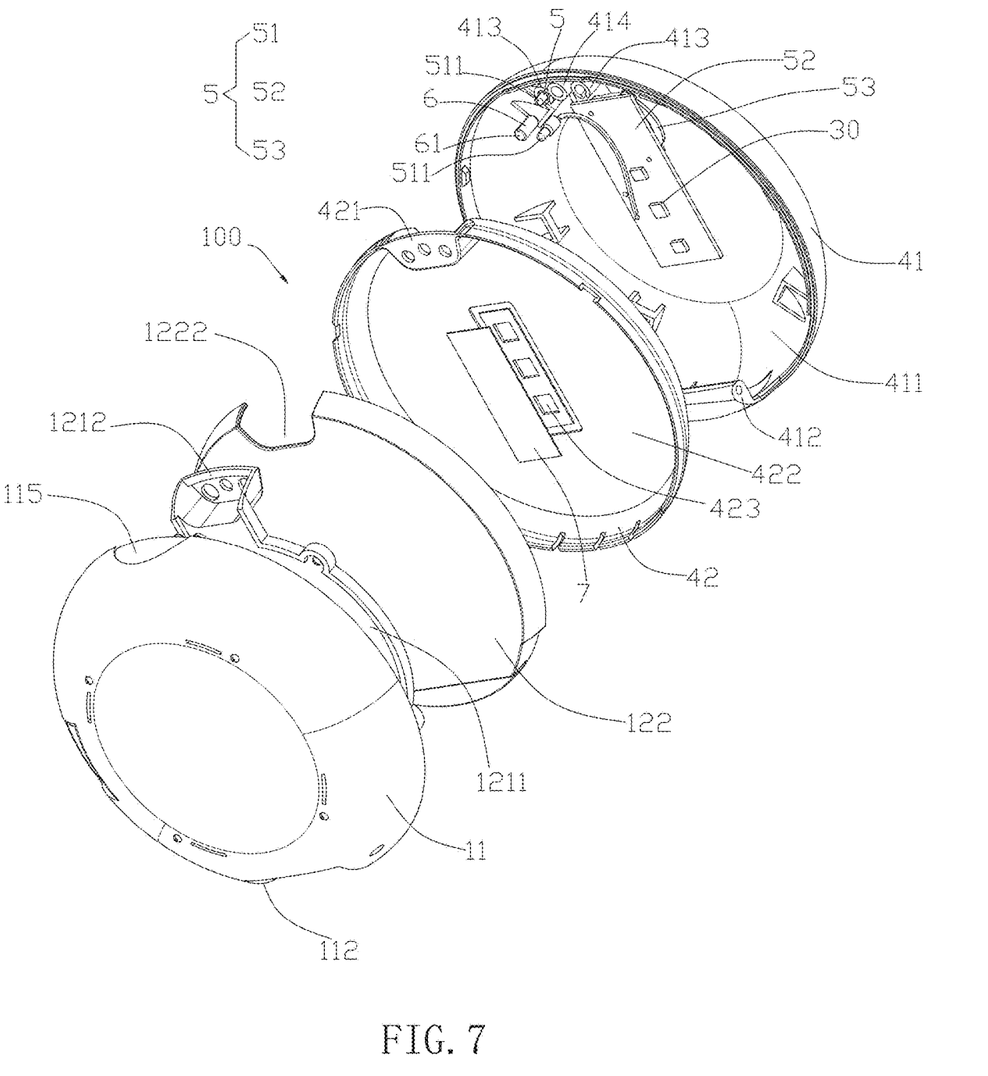
FIG. 7 is an isometric exploded view of the portable UV-sanitizing box in FIG. 7, viewed from another aspect.

In the embodiment, one end of the lower shell 10 is connected with the upper shell 20 in an articulated manner. The lower shell 10 includes a first casing 1, a first conductive component 2 disposed on the first casing 1, and a first joint. The first conductive component 2 includes two first conductive terminals 21, a first printed circuit board assembly 22 and a charging interface 23. The first conductive terminals 21 are electrically connected to the first printed circuit board assembly 22 by wires. The first printed circuit board assembly 22 is electrically connected to the charging interface 23. The first joint and the first conductive terminal 21 are arranged in a staggered manner from each other. One end of the first conductive terminal 21 has a first terminal contact surface 211. The first joint is a first magnetic member 3. The first magnetic element 3 has a first magnetic contact surface 31.

Figure 8:
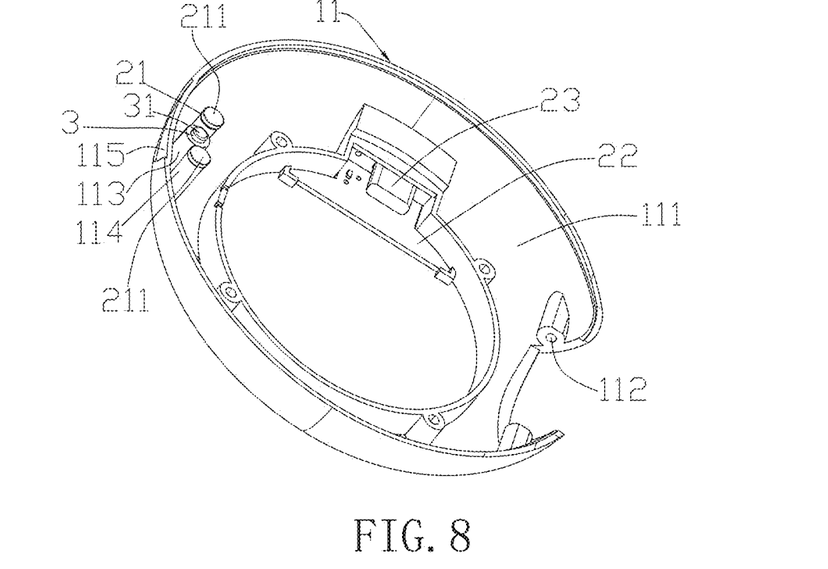
FIG. 8 is an isometric view of a first outer housing of the lower shell in FIG. 6.

The first casing 1 is provided with a first mounting portion 1212 protruding inward relative to the edge of the accommodating cavity, and the first conductive terminal 21 is provided on the first mounting portion 1212. The first housing 1 includes a first outer housing 11.

The first outer housing 11 is recessed with a first installation cavity 111, and both the first printed circuit board assembly 22 and the charging interface 23 are installed in the first installation cavity 111. The first outer housing 11 is provided with a first pivoting portion 112. The first mounting portion 1212 and the first pivoting portion 112 are respectively located on the front and rear sides of the UV-sanitizing box 100. A groove 115 is recessed on the outer surface of one side of the first outer housing 11 close to the first mounting portion 1212 to facilitate the user to apply force to the upper shell 20. The first outer housing 11 is provided with a first terminal mounting post 113 and a first butt mounting post 114 protruding from the first installation cavity 111. Both the first terminal mounting post 113 and the first butt mounting post 114 protrude upward from the cavity wall of the first installation cavity 111 toward the accommodating cavity. The first conductive terminal 21 is mounted on the first terminal mounting post 113. The first joint is mounted on the first butt mounting post 114.

Figure 9:
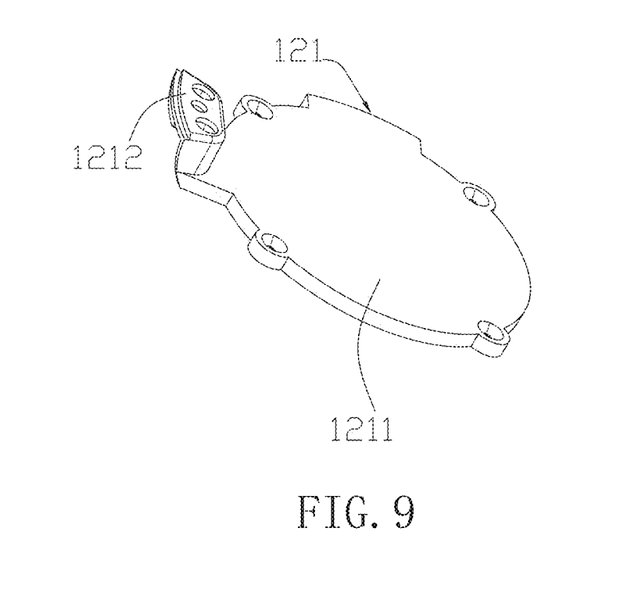
FIG. 9 is an isometric view of a carrier plate of the lower shell in FIG. 6.
Figure 10:
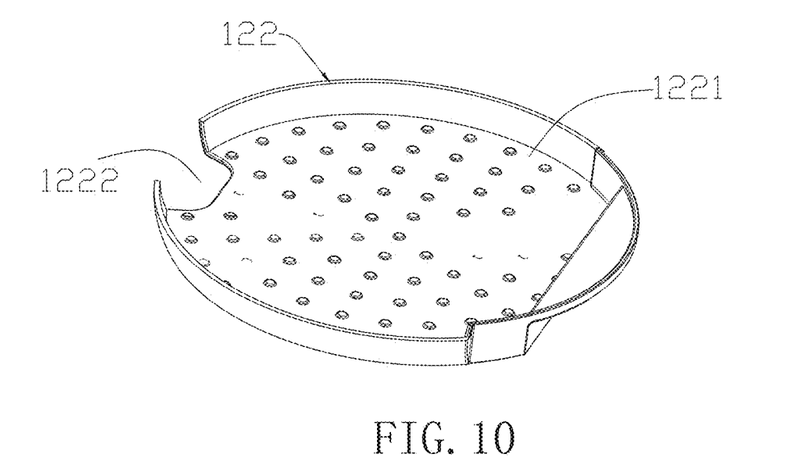
FIG. 10 is an isometric view of a tray of the lower shell in FIG. 6.

A first accommodating cavity 1221 is protruded with the first mounting portion 1212, and the first terminal mounting post 113 and the first butt mounting post 114 are both mounted in the first mounting portion 1212. The first mounting portion 1212 is exposed in the first accommodating cavity 1221 and both the first conductive terminal 21 and the first engaging member are exposed in the first mounting portion 1212. The first outer housing 11 is provided with a carrying plate 121 and a tray 122 inside. The carrying plate 121 includes a main body 1211 and the first mounting part 1212 connected with the main body 1211. The main body 1211 is fastened to the first casing 11 and located between the first casing 11 and the tray 122. The tray 122 is concavely provided with the first accommodating cavity 1221 and a recess 1222 for accommodating the first mounting portion 1212. The tray 122 is approximately oblong or circular bowl-shaped, and includes a bottom with a textured, a sidewall extending from the bottom. In the embodiment, the tray 122 may be made of materials such as silicone, rubber, or plastic. A surface of the tray 122 is also provided with a texture pattern that enhances the friction force to prevent the sterilized parts such as ear studs, dentures, braces, or the brush head of a toothbrush from sliding in the sterilization box 100.

Figure 11:
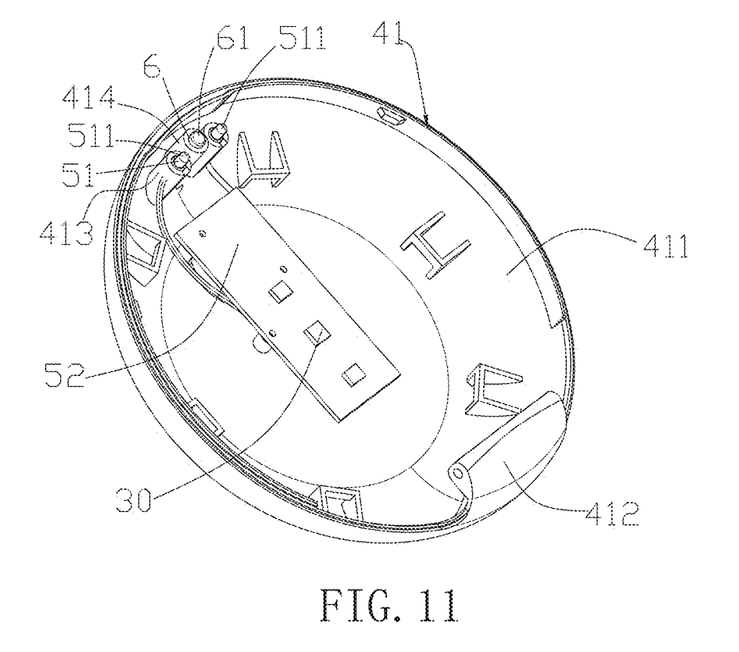
FIG. 11 is an isometric view of an upper shell of the portable UV-sanitizing box in FIG. 5
Figure 12:
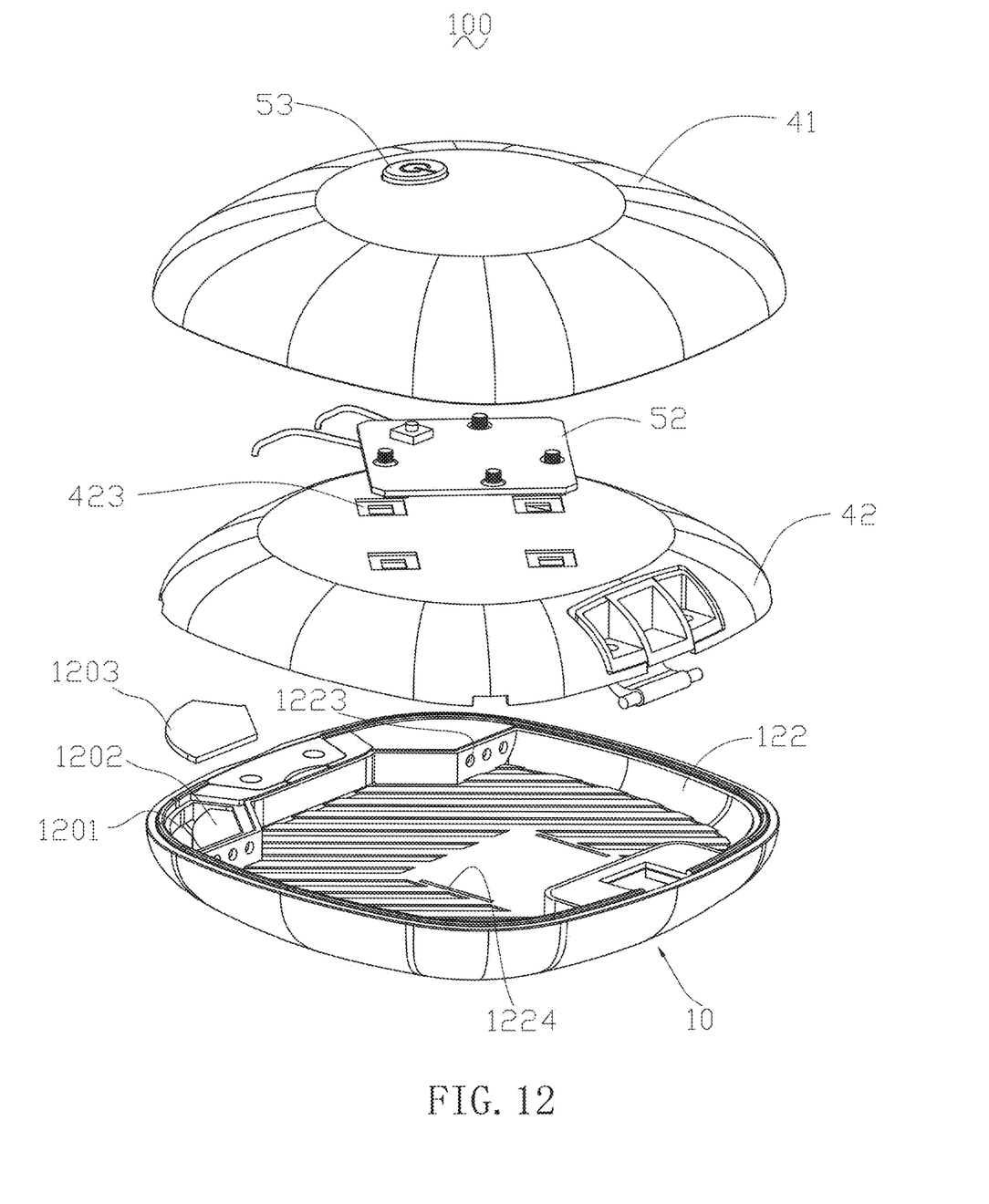
FIG. 12 is an isometric view of a portable UV-sanitizing box in accordance with a second embodiment of the present disclosure.
Figure 13:
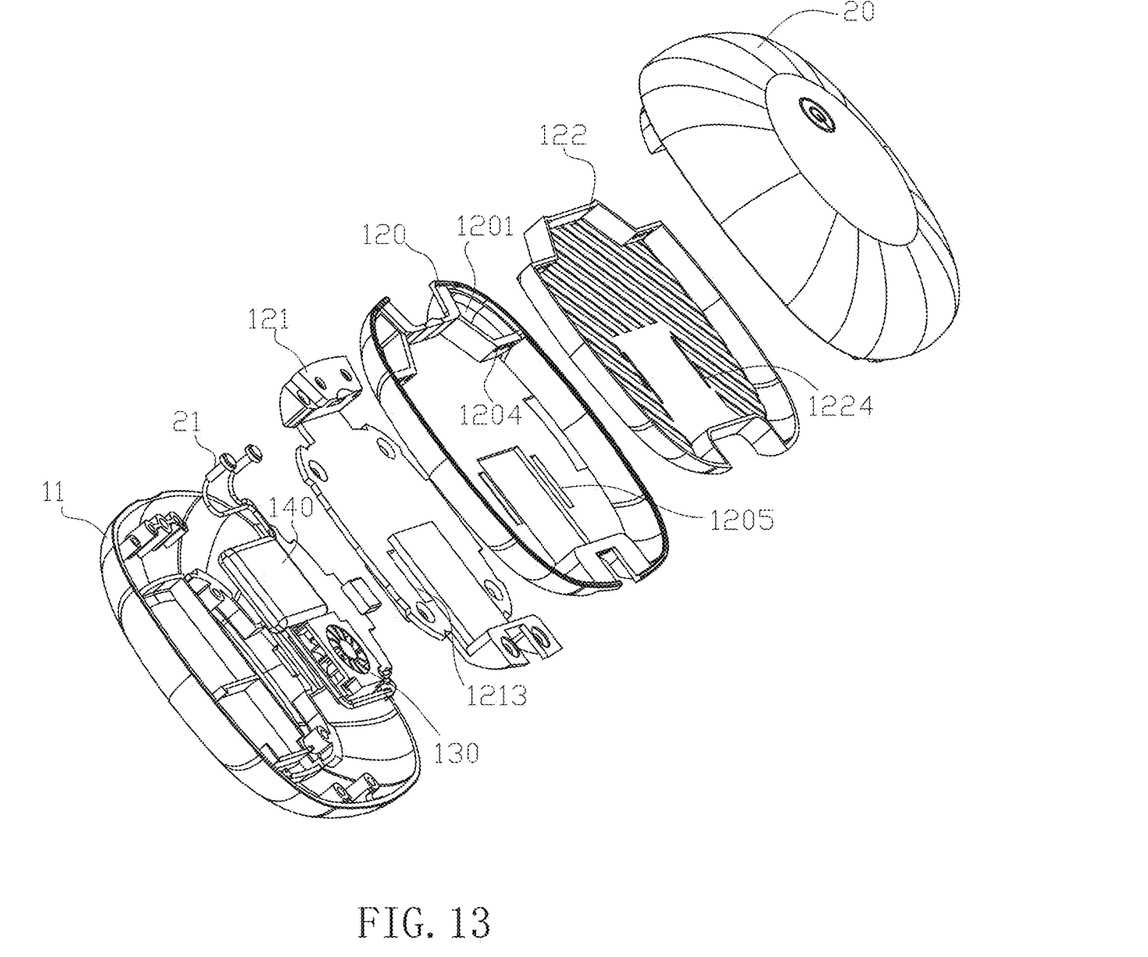
FIG. 13 is an isometric exploded view of the portable UV-sanitizing box in FIG. 12.
Figure 14:
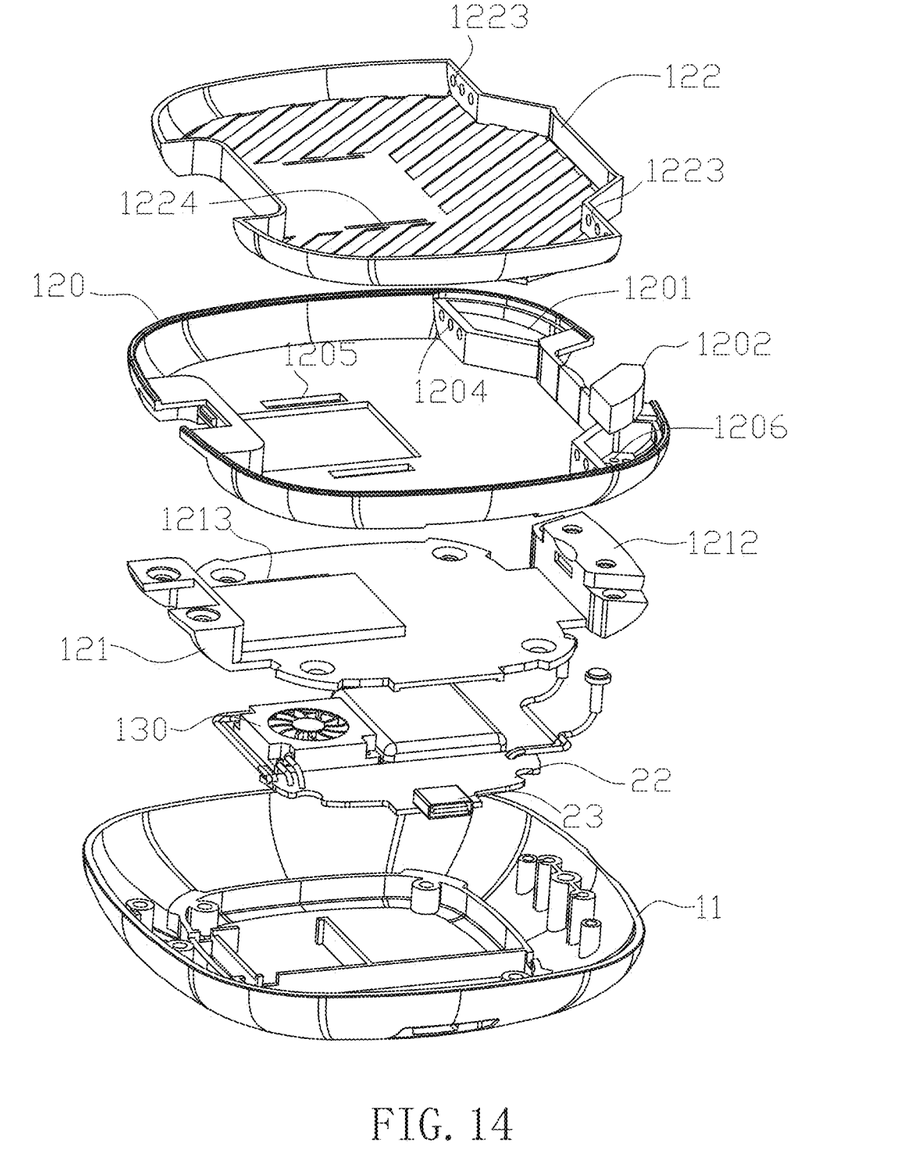
FIG. 14 is an isometric exploded view of a lower shell of the portable UV-sanitizing box in FIG. 12.
Figure 15:
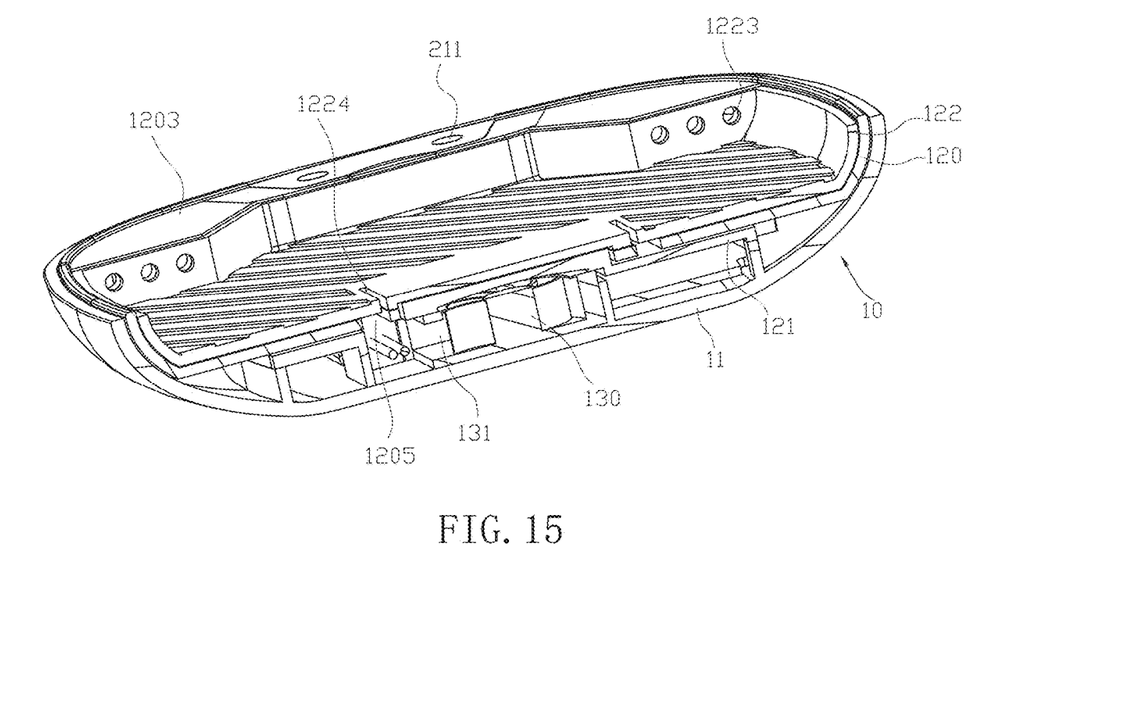
FIG. 15 is a cross-sectional view of the lower shell in FIG. 12.

Similarly, the upper shell 20 includes a second casing 4, a second conductive component 5 and a second joint disposed on the second casing 4. The sterilizing component 30 is electrically connected to the second conductive component 5. When the lower shell 10 and the upper shell 20 are opened, the accommodating cavity is exposed, the first conductive component 2 and the second conductive component 5 are not electrically connected to form a loop, so that the sterilizing assembly 30 is not electrically connected. When the lower shell 10 and the upper shell 20 are closed, the accommodating cavity is shielded, the first conductive component 2 and the second conductive component 5 are electrically connected and form a loop to make the sterilizing assembly 30 conducts and works in the accommodating cavity. In this way, it is ensured that when the lower shell 10 and the upper shell 20 are opened, the sterilizing assembly 30 will not harm the human body, which is safer.

The second conductive component 5 includes two second conductive terminals 51, a second printed circuit board assembly 52 and a switching button 53. The second conductive terminal 51 is electrically connected to the second printed circuit board assembly 52 by wires. The switching button 53 is electrically connected to the second printed circuit board assembly 52. The switching button 53 is exposed on the upper shell 20 for convenience. The second joint and the second conductive terminal 51 are arranged in a staggered manner. More further, the first joint is not disposed on a connection line of the two first conductive terminals 21, and the second joint is not disposed on a connection line of the two second conductive terminals 51. When the lower shell 10 and the upper shell 20 are closed, the first joint, the two first conductive terminals 21 and the first joint and the two first conductive terminals 21 forming a triangular docking point, the contact is more stable. The first joint is disposed between the two first conductive terminals 21. The second joint is disposed between the two second conductive terminals 51, so that the first conductive terminal 21 and the second conductive terminal 51 receive a more balanced force when they are in contact with each other.

The second conductive terminal 51 has a second terminal contact surface 511. When the lower case body 10 and the upper case body 20 are opened, the first terminal contact surface 211 and the second terminal contact surface 511 are not in contact. When the lower case body 10 and the upper case body 20 are closed, the first terminal contact surface 211 and the second terminal contact surface 511 abut together. Further, the size of the first terminal contact surface 211 is larger than 1.5 times the size of the second terminal contact surface 511. The size of the first terminal contact surface 211 and the size of the second terminal contact surface 511 are the largest lengths in each direction. In this embodiment, the first terminal contact surface 211 and the second terminal contact surface 511 are both circular. In other embodiments, the first terminal contact surface 211 and the second terminal contact surface 511 may also be rectangular or irregular in shape.

The second joint is the second magnetic member 6. The second magnetic member 6 has a second magnetic contact surface 61, and the size of the second magnetic contact surface 61 is substantially the same as the size of the second magnetic contact surface 61 and the size of the second terminal contact surface 511 is smaller than the size of the first terminal contact surface 211. When the lower shell 10 and the upper shell 20 are opened, the first magnetic contact surface 31 and the second magnetic contact surface 61 are not in contact. When the lower shell 10 and the upper shell 20 are closed, the first magnetic contact surface 31 and the second magnetic contact surface 61 are in magnetic contact with each other.

The function of the first joint and the second joint is to stably connect the lower shell 10 and the upper shell 20 to prevent the lower box body 10 and the upper box body 20 from being separated.

The two first conductive terminals 21 and the two second conductive terminals 51 are both positive and negative terminals and are connected in one-to-one correspondence. When the lower case body 10 and the upper case body 20 are opened, the first joint and the second joint are not in contact, and the first conductive terminal 21 and the second conductive terminal 51 are not in contact catch. When the lower shell 10 and the upper shell 20 are closed, the first conductive terminal 21 and the second conductive terminal 51 abut together.

The second housing 4 is provided with a second mounting portion 421 protruding inward, and the second conductive terminal 51 is provided on the second mounting portion 421. In other embodiments, the first casing 1 or the second casing 4 may be provided with the first mounting portion 1212 or the second mounting portion 421. The second casing 4 includes a second outer housing 41 and a second inner housing 42. The second outer housing 41 is recessed with a second installation cavity 411, and the second inner housing 42 is installed in the second installation cavity 411 and is snap-connected to the second outer housing 41. The second printed circuit board assembly 52 and the sterilizing assembly 30 are both installed in the second installation cavity 411 and located between the second outer housing 41 and the second inner housing 42. The second outer housing 41 is provided with a second pivoting portion 412 pivotally connected to the first pivoting portion 112. The second outer housing 41 is provided with a second terminal mounting post 413 and a second abutting mounting post 414 protruding toward the accommodating cavity relative to the cavity wall of the second mounting cavity 411. The second terminal mounting post 413 and the second abutting mounting post 414 protrude downward from the cavity wall of the second mounting cavity 411. The second conductive terminal 51 is mounted on the second terminal mounting post 413.

The second inner housing 42 is concavely provided with a second accommodating cavity 422 and convexly provided with the second mounting portion 421. The second terminal mounting post 413 is mounted in the second mounting portion 421. The second mounting portion 421 is exposed from the second accommodating cavity 422 and the second conductive terminal 51 is exposed from the second mounting portion 421. When the lower shell 10 and the upper shell 20 are closed, the first accommodating cavity 1221 and the second accommodating cavity 422 form the accommodating cavity.

In this embodiment, the sterilizing assembly 30 is an ultraviolet ray lamp assembly. The second inner shell 42 defines at least one light-transmitting hole 423 for the ultraviolet ray lamp assembly to irradiate the accommodating cavity through the light-transmitting hole 423. A light-transmitting sheet 7 is attached to the side of the second inner shell 42 facing the second accommodating cavity 422 to shield the light-transmitting hole 423.

When personal items such as dentures are placed in the UV sanitizing box 100 for sterilization treatment, user may apply force to the second casing 4 in the groove 115 to open and expose the upper shell 20. At this time, the first mounting portion 1212 and the second mounting portion 421 are separated, the first magnetic member 3 and the second magnetic member 6 are separated and not in contact, and the first conductive terminal 21 and the first two conductive terminals 51 are not in contact with each other, so that no electrical circuit is formed to electrically conduct the sterilizing assembly 30. After the object is placed, the upper shell 20 and the lower shell 10 are closed, the first magnetic member 3 and the second magnetic member 6 are magnetically attracted, and the first conductive terminal 21 in contact with the second conductive terminal 51, the controlling circuit is turned on by pressing the switching button 53, thereby controlling the sterilizing assembly 30 to conduct sterilization processing for the object to be sterilized.

Referring to FIGS. 12 to 15, another embodiment of the portable UV-sanitizing box 100 has the same structure as the first embodiment. The portable UV-sanitizing box 100 also includes a lower shell 10 and an upper shell 20. The upper shell 20 includes a second outer housing 41 and a second inner housing 42, and the switching button 53 is exposed on the upper surface of the second outer housing 41. A second printed circuit board assembly 52 is provided between the second outer housing 41 and the second inner housing 42, and the second printed circuit board assembly 52 is provided with UV light sources arranged in a matrix. The second inner housing 42 is provided with light-transmitting holes 423 corresponding to the UV light sources arranged in a matrix for transmitting light. The difference between this embodiment and the first embodiment is that the number of UV light sources arranged in the matrix is four, which are arranged symmetrically in a rectangular shape.

Similarly, the lower shell 10 of this embodiment and the first embodiment also includes a first outer housing 11, a carrier plate 121 and a tray 122. The unmentioned structure is the same as that of the first embodiment. In this embodiment, the spatial position of the tray 122 is the same as that of the first embodiment, that is, the tray 122 is accommodated in the carrier plate 121. The difference is that a fan element 130 electrically connected to the first printed circuit board assembly 22 is provided between the first outer housing 11 and the carrier board 121, and a first inner housing 120 is provided between the carrier board 121 and the tray 122. Preferably, the first printed circuit board assembly 22 is installed on the back of the carrier board 121, that is, the fan element 130 is installed on a surface of the carrier board 121 away from the upper shell 20, and is driven by a battery 140 on the side. The fan element 130 is a miniature fan with fan blades. The carrier plate 121 has an air outlet 131 matched with the fan element 130. The direction of the air outlet 131 is parallel to the direction of the rotating surface of the fan blade of the fan element 130. The carrier plate 121 is provided with a ventilation slot 1213 that communicates with the air outlet 131. The first inner housing 120 provided above the carrier board 121 has a shape matching with the first outer housing 11, and the first inner housing 120 is provided with an air circulation slits 1205. In addition, the first inner housing 120 is further provided with an adsorption cavity 1201 adjacent to the first mounting portion 1212, and an activated carbon 1202 is loaded in the adsorption cavity 1201. The adsorption chamber 1201 is provided with a cover 1203 to prevent the activated carbon 1202 from falling off. An air holes 1204 and 1206 communicating with the adsorption chamber 1201 are respectively provided on the peripheral side walls of the adsorption chamber 1201. In this embodiment, the number of the adsorption chambers 1201 is two. The adsorption chambers 1201 are respectively arranged on both sides of the first mounting portion 1212. Furthermore, the tray 122 is provided with a through hole 1223 corresponding to the position of the air hole 1204, and the bottom of the tray 122 is provided with an air slit 1224 corresponding to the position of the air circulation slit 1205. When the fan element 130 on the upper part of the carrier plate 121 works, the air inside the sanitizing box 100 is driven to form an air circulation through the circulation air slit 1205, the air slit 1224, the through hole 1223, the adsorption cavity 1201, and the air hole 1206. The activated carbon 1202 absorbs the odor of the objects to be sterilized such as braces and dentures in the first accommodating cavity 1221, and improves the elimination of odor inside the sterilization box. In other embodiment, the adsorption cavity 1201 is provided on the tray 122, and an activated carbon 1202 is arranged in the adsorption cavity of the tray 122.

While the present disclosure has been described with reference to a specific embodiment, the description of the disclosure is illustrative and is not to be construed as limiting the disclosure. Various of modifications to the present disclosure can be made to the exemplary embodiment by those skilled in the art without departing from the true spirit and scope of the disclosure as defined by the appended claims.

The invention claimed is:

1. A portable UV-sanitizing box comprising:
   a lower shell having a first outer housing, a carrying plate, a tray configured to carry items to be sterilized;
   an upper shell hinged to the lower shell, having a second outer housing and a second inner housing;
   a sterilizing assembly having an ultraviolet ray lamp assembly arranged on the upper shell, a switching button, and a first printed circuit board assembly arranged on the lower shell; and wherein
   a first conductive component arranged on the lower shell has two first conductive terminals for electrically connecting to the first printed circuit board assembly, and a first magnetic member adjacent to the first conductive component is mounted on the lower shell;
   a second conductive component arranged on the upper shell has two second conductive terminals for electrically connecting to the ultraviolet ray lamp assembly, a second magnetic member corresponding to the first magnetic member adjacent to the second conductive component is mounted on the lower shell, and the second magnetic member and the first magnetic member are magnetically attracted to each other;
   when the upper shell and the lower shell are snapped together, the first conductive member and the second conductive member are in contact with each other and are configured to be in electrical communication, so that the sterilizing assembly works;
   when the upper shell is opened, the first conductive member and the second conductive member are not in electrical contact with each other.

2. The portable UV-sanitizing box as described in claim 1, wherein the first magnetic member is located between the two first conductive terminals, and the second magnetic member is located between the two second conductive terminals.

3. The portable UV-sanitizing box as described in claim 2, wherein the first magnetic member is offset from the connecting line between the two first conductive terminals.

4. The portable UV-sanitizing box as described in claim 1, wherein the carrying plate has a first mounting portion protruding inwardly relative to the edge of the lower housing, the first conductive component and the first magnetic member are mounted on the first mounting portion.

5. The portable UV-sanitizing box as described in claim 4, wherein the tray includes a concave first accommodating cavity and a recess for accommodating the first mounting portion.

6. The portable UV-sanitizing box as described in claim 5, wherein an adsorption cavity is provided on the tray, an activated carbon is arranged in the adsorption cavity, and the adsorption cavity is communicated with the first accommodating cavity of the tray.

7. The portable UV-sanitizing box as described in claim 6, wherein the tray is made of plastic, silicone, rubber materials.

8. The portable UV-sanitizing box as described in claim 1, wherein the switching button is exposed on the upper shell and is electrically connected to a second printed circuit board assembly of the second conductive component.

9. The portable UV-sanitizing box as described in claim 1, wherein a first inner housing is provided between a carrier board and the tray for loading activated carbon.

10. The portable UV-sanitizing box as described in claim 9, wherein an adsorption cavity is provided on the first inner housing, an activated carbon is loaded in the adsorption cavity.

11. The portable UV-sanitizing box as described in claim 10, wherein the number of adsorption chambers is at least two, which are arranged symmetrically.

12. The portable UV-sanitizing box as described in claim 9, wherein a fan element is installed on a surface of a carrier board away from the upper shell for promoting internal air circulation of the sanitizing box.

13. The portable UV-sanitizing box as described in claim 12, wherein the carrying plate has an air outlet which is matched with the fan element.

14. The portable UV-sanitizing box as described in claim 13, wherein a ventilation slot is provided on the carrying plate for communicating with the air outlet.

15. The portable UV-sanitizing box as described in claim 14, wherein the first inner housing is provided with an air circulation slits for communicating with ventilation slot and the adsorption cavity.

* * * * *